US009345250B2

(12) United States Patent
Hayashi et al.

(10) Patent No.: US 9,345,250 B2
(45) Date of Patent: May 24, 2016

(54) METHOD FOR PREPARING SOLUBILIZED COMPOSITION CONTAINING OIL-SOLUBLE SUBSTANCE

(75) Inventors: Akihito Hayashi, Matsusaka (JP); Chie Kato, Matsusaka (JP); Namiko Takahashi, Matsusaka (JP); Nobutoshi Hamaguchi, Matsusaka (JP); Hen-Sik Koh, Matsusaka (JP)

(73) Assignee: TSUJI OIL MILL CO., LTD., Mie (JP)

( * ) Notice: Subject to any disclaimer, the term of this patent is extended or adjusted under 35 U.S.C. 154(b) by 1248 days.

(21) Appl. No.: 11/898,994

(22) Filed: Sep. 18, 2007

(65) Prior Publication Data

US 2008/0070992 A1 Mar. 20, 2008

(30) Foreign Application Priority Data

Sep. 20, 2006 (JP) ................. 2006-255041

(51) Int. Cl.
| A61K 47/26 | (2006.01) |
| A23L 2/52 | (2006.01) |
| A23D 9/00 | (2006.01) |
| A23D 9/013 | (2006.01) |
| A23L 1/035 | (2006.01) |
| A61K 8/31 | (2006.01) |
| A61K 8/34 | (2006.01) |
| A61K 8/35 | (2006.01) |
| A61K 8/37 | (2006.01) |
| A61K 8/39 | (2006.01) |
| A61K 8/55 | (2006.01) |
| A61K 8/60 | (2006.01) |
| A61K 8/92 | (2006.01) |
| A61Q 19/00 | (2006.01) |

(52) U.S. Cl.
CPC ........ *A23D 9/00* (2013.01); *A23D 9/013* (2013.01); *A23L 1/035* (2013.01); *A61K 8/31* (2013.01); *A61K 8/34* (2013.01); *A61K 8/35* (2013.01); *A61K 8/37* (2013.01); *A61K 8/39* (2013.01); *A61K 8/553* (2013.01); *A61K 8/60* (2013.01); *A61K 8/922* (2013.01); *A61Q 19/00* (2013.01)

(58) Field of Classification Search
None
See application file for complete search history.

(56) References Cited

U.S. PATENT DOCUMENTS

| 4,343,823 | A | | 8/1982 | Todd, Jr. et al. |
| 4,608,267 | A | * | 8/1986 | Dutilh ........................... 426/662 |
| 4,849,132 | A | | 7/1989 | Fujita et al. |
| 5,466,719 | A | * | 11/1995 | Jakobson et al. ............ 514/785 |
| 6,140,375 | A | * | 10/2000 | Nagahama et al. .......... 516/73 |
| 6,193,986 | B1 | | 2/2001 | Sakurada |
| 6,451,339 | B2 | * | 9/2002 | Patel et al. ................... 424/451 |
| 6,720,016 | B2 | * | 4/2004 | Yamaguchi et al. .......... 426/74 |
| 7,166,311 | B2 | * | 1/2007 | Ikehara et al. ............... 424/757 |
| 2004/0247678 | A1 | | 12/2004 | Toyoda et al. |
| 2005/0260145 | A1 | * | 11/2005 | Leigh et al. .................. 424/63 |
| 2008/0038210 | A1 | * | 2/2008 | Yano et al. ................... 424/49 |

FOREIGN PATENT DOCUMENTS

| EP | 1 806 125 | | 7/2007 |
| EP | 2 062 574 | | 5/2009 |
| GB | 2 070 910 | | 9/1981 |
| JP | 63-166425 | | 7/1988 |
| JP | 7-100355 | | 4/1995 |
| JP | 7-147899 | | 6/1995 |
| JP | 07-147899 | * | 6/1995 |
| JP | 07147899 | * | 7/1995 |
| JP | 8-205771 | | 8/1996 |
| JP | 9-168369 | | 6/1997 |
| JP | 10-43573 | | 2/1998 |
| JP | 10-66860 | | 3/1998 |
| JP | 10-084887 | | 4/1998 |
| JP | 10-120933 | | 5/1998 |
| JP | 10-182493 | | 7/1998 |
| JP | 11-332463 | | 12/1999 |
| JP | 2001-48743 | | 2/2001 |
| JP | 2004-339086 | | 12/2004 |
| WO | WO/2006/043621 | * | 4/2006 |

OTHER PUBLICATIONS

JAOCS, vol. 66, No. 5, pp. 714-717 (Juneja et al) 1989.*
International Journal of Pharmaceuticals, vol. 137, pp. 177-186 (Thevenin et al) 1996.*
Cruces et al., JACOS 78(5), 541-546, 2001, Improved Synthesis of Sucrose Fatty Acid Monoesters.*
European Search Report issued Dec. 5, 2007 in the corresponding application.
European Office Action issued Aug. 24, 2010 in corresponding European Application No. 07 116 593.0.
Japanese Office Action issued Oct. 19, 2010 in corresponding Japanese Application No. 2006-255041.
European Office Action issued Oct. 20, 2011 in corresponding European Application No. 07 116 593.0.

* cited by examiner

*Primary Examiner* — Tigabu Kassa
(74) *Attorney, Agent, or Firm* — Wenderoth, Lind & Ponack, L.L.P.

(57) ABSTRACT

The present invention provides a method for preparing a solubilized composition containing an oil-soluble substance having both acid and heat resistance, including:
the step of dissolving an oil-soluble substance and two or three emulsifiers selected from
(1) an emulsifier E1 comprising an ester of a fatty acid having an HLB of not less than 10 and not more than 14 carbon atoms with a polyglycerol having a polymerization degree of not less than 3,
(2) an emulsifier E2 comprising an ester of a fatty acid having an HLB of not less than 10 and not more than 14 carbon atoms with sucrose, or
(3) an emulsifier E3 comprising lecithin in which phosphatidylcholine accounts for not less than 50% and/or lysolecithin in which lysophosphatidylcholine accounts for not less than 50% of a phospholipid content in (a) ethanol or (b) a mixed solvent of ethanol with at least one selected from the group consisting of acetone, hexane, and ethyl acetate to prepare a transparent solution; and
the step of distilling the solvent off from the transparent solution.

11 Claims, No Drawings

METHOD FOR PREPARING SOLUBILIZED COMPOSITION CONTAINING OIL-SOLUBLE SUBSTANCE

BACKGROUND OF THE INVENTION

1. Field of the Invention

The present invention relates to a method for preparing a solubilized composition containing an oil-soluble substance having both acid and heat resistance, the composition prepared by the method, and foods and drinks and cosmetics containing the composition. In particular, the present invention relates to a method for preparing a solubilized composition containing an oil-soluble substance, which is capable of keeping the oil-soluble substance in a uniform and stable solubilized state without its deposition or floating when a food and drink, or a cosmetic added with the composition is stored for a long time, and has both excellent acid and heat resistance necessary when being added to foods and drinks. The present invention also relates to the composition prepared by the method of the present invention, and foods and drinks and cosmetics containing the composition.

2. Description of the Related Art

In the fields of foods and drinks and cosmetics, commercial products in the liquid state at ambient temperature have been conventionally added with oil-soluble substances such as colorants, flavoring agents, oils and fats, fat-soluble vitamins, bioactive substances, seasonings, antioxidants, and preservatives. However, many of liquid preparations of foods and drinks and cosmetics are aqueous. To add an oil-soluble substance to these aqueous foods and drinks and cosmetics, there have been various known compositions and methods for preparing them. An example of the composition is an emulsion of an oil-soluble substance in an aqueous medium. Examples of the emulsion include: a carotenoid-based pigment-solubilized liquid preparation for foods capable of coloring aqueous foods and drinks (JP-A-10-120933); a composition containing a sucrose fatty acid ester, a $C_{4-20}$ monohydric alcohol, an oily component, and water at a specific weight ratio (JP-A-10-43573 and JP-A-10-66860); a water-soluble composition containing a uniformly emulsified or solubilized oil and fat prepared by mixing an oil and fat and a lower alcohol solution containing at least one selected from the group consisting of monoesters of polyglycerols having a polymerization degree of 4 to 10 with capric acid, lauric acid, oleic acid and linoleic acid and an enzymatically decomposed lecithin with water or an aqueous solution of a sugar alcohol, and removing the lower alcohol from the mixture (JP-A-7-147899); an oil-and-fat-containing water-soluble composition in a emulsified or solubilized state containing at least one polyglycerol fatty acid ester selected from monoesters of polyglycerols having a polymerization degree of not less than 10 with $C_{8-18}$ fatty acids, a sucrose fatty acid ester containing not less than 90% of a monoester of sucrose with a fatty acid, an oil and fat and residual parts of water (JP-A-8-205771); a solubilized oil and fat composition containing 0.003 to 50% by weight of at least one polyglycerol fatty acid monoester selected from monoesters of polyglycerol having an average polymerization degree of 6 to 10 with $C_{12-14}$ saturated fatty acids, 0.05 to 20% by weight of an oil and fat, and residual parts of water and food additives (JP-A-9-168369); an oil-soluble substance-solubilized composition containing 0.01 to 30% by weight of a monoester of a polyglycerol fatty acid having an average polymerization degree of not less than 5 with myristic or oleic acid, 40 to 80% by weight of a polyhydric alcohol, 0.01 to 20% by weight of an oil-soluble substance, and residual parts of water (JP-A-10-084887); and an oil-soluble substance-solubilized composition containing (A) 0.05 to 30% by weight of an oil-soluble substance, (B) 0.003 to 50% by weight of polyglycerol fatty acid monoester of a polyglycerol having an average polymerization degree of 6 to 15 with a $C_{12-18}$ saturated or monounsaturated fatty acid, (C) 0.0001 to 1% by weight of lecithin, and water (JP-A-11-332463). Any of methods for preparing these compositions includes emulsifying an oil-soluble substance in an aqueous medium, and fragmentating the oil-soluble substance into the nano-scale order with, for example, an emulsifying apparatus or a high-pressure homogenizer which applies strong shearing force. However, when the compositions prepared by the methods are added into cosmetics or foods and drinks, these cosmetics or foods and drinks do not sufficiently satisfy solubility, transparency, stability, heat resistance, and particularly acid resistance. In addition, the compositions are emulsions with aqueous media, and therefore have a compositional limitation on an amount added in commercial products.

There are known other methods for preparing an oil-soluble substance-solubilized composition, including preliminarily heating an oil-soluble substance and an emulsifier to form a uniform mixture, and adding the mixture to an aqueous medium (JP-A-7-100355, JP-A-10-182493, and JP-A-2004-339086). However, compositions prepared by the methods also do not satisfy solubility, transparency, stability, heat resistance, and acid resistance, when added to aqueous media.

SUMMARY OF THE INVENTION

An object of the present invention is to provide a method for preparing a solubilized composition containing an oil-soluble substance having both excellent acid and heat resistance, capable of easily keeping the oil-soluble substance in a uniform and stable solubilized state in an aqueous medium, such as an aqueous food and drink and an aqueous cosmetic (hereinafter, also referred to simply as an aqueous medium), without using an emulsifier or a high-pressure homogenizer which applies strong shearing force, when the composition is added to the aqueous medium. Another object of the present invention is to provide the composition prepared by the above method.

As a result of intensive investigations to achieve the above-mentioned objects, the present inventors have found that a solubilized composition having both acid and heat resistance can be obtained by transparently dissolving an oil-soluble substance and two or more emulsifiers of (1) a specific polyglycerol fatty acid ester (emulsifier E1), (2) a specific sucrose fatty acid ester (emulsifier E2), and (3) a specific lecithin containing an increased amount of phosphatidylcholine and/or lysophosphatidylcholine (emulsifier E3) in a solvent containing ethanol, and removing the solvent off. The present inventors have further studied and accomplished the present invention.

That is, the present invention provides:

(I) a method for preparing a solubilized composition containing an oil-soluble substance having both acid and heat resistance, including:

the step of dissolving an oil-soluble substance and two or three emulsifiers selected from (1) an emulsifier E1 comprising an ester of a fatty acid having an HLB of not less than 10 and not more than 14 carbon atoms with a polyglycerol having a polymerization degree of not less than 3, (2) an emulsifier E2 comprising an ester of a fatty acid having an HLB of not less than 10 and not more than 14 carbon atoms with sucrose, or (3) an emulsifier E3 comprising lecithin in which phosphatidylcholine accounts for not less than 50% and/or lysolecithin in which lysophosphatidylcholine accounts for not less than 50% of a phospholipid content in (a) ethanol or (b) a mixed solvent of ethanol with at least one selected from the group consisting of acetone, hexane, and ethyl acetate to prepare a transparent solution; and the step of distilling the solvent off from the transparent solution;

(II) the method according to (I), wherein the solvent (a) or (b) is ethanol or a mixed solvent of ethanol with acetone or hexane, and a percentage of ethanol in the solvent is 50 to 100 (V/V) %;

(III) the method according to (I), wherein the emulsifiers are the emulsifiers E1, E2, and E3, and contents of the emulsifiers to 1 part by mass of the oil-soluble substance are:

0.1 to 50 parts by mass for the emulsifier E1,
0.1 to 30 parts by mass for the emulsifier E2, and
0.1 to 20 parts by mass for the emulsifier E3;

(IV) the method according to (I), further including:

the step of adding a polyhydric alcohol to the transparent solution in an amount of not more than 50 parts by mass to 1 part by mass of the oil-soluble substance, between the step of preparing the transparent solution and the step of distilling the solvent off;

(V) a solubilized composition containing an oil-soluble substance having both acid and heat resistance, which is characterized in that the composition is prepared by the method according to (I);

(VI) the composition according to (V), further containing ethanol in a proportion of not more than 50 parts by mass to 1 part by mass of the oil-soluble substance;

(VII) a food and drink containing the composition according to (V);

(VIII) a cosmetic containing the composition according to (V);

(IX) a method for solubilizing an oil-soluble substance, comprising adding the composition according to (V) to a food and drink, or a cosmetic; and (X) use of a composition as a solubilizing agent for solubilizing an oil-soluble substance in a food and drink or a cosmetic, wherein the composition is prepared by a method, including:

the step of dissolving an oil-soluble substance and two or three emulsifiers selected from (1) an emulsifier E1 comprising an ester of a fatty acid having an HLB of not less than 10 and not more than 14 carbon atoms with a polyglycerol having a polymerization degree of not less than 3, (2) an emulsifier E2 comprising an ester of a fatty acid having an HLB of not less than 10 and not more than 14 carbon atoms with sucrose, or (3) an emulsifier E3 comprising lecithin in which phosphatidylcholine accounts for not less than 50% and/or lysolecithin in which lysophosphatidylcholine accounts for not less than 50% of a phospholipid content in (a) ethanol or (b) a mixed solvent of ethanol with at least one selected from the group consisting of acetone, hexane, and ethyl acetate to prepare a transparent solution; and the step of distilling the solvent off from the transparent solution.

The method for preparing a solubilized composition containing an oil-soluble substance of the present invention includes the following steps 1 and 2.

Step 1: transparently dissolving an oil-soluble substance and two or three emulsifiers selected from emulsifier E1, E2, or E3 into the following solvent (a) or (b):

(a) ethanol;
(b) a mixed solvent of ethanol with one or more solvent(s) selected from acetone, hexane, and ethyl acetate.

Step 2: distilling off the solvent dissolved in Step 1.

The oil-soluble substance used in Step 1 may be any substance that is insoluble or hardly soluble in water, and easily soluble in oil without specific limitation. Examples of such oil-soluble substance include colorants, flavoring agents, oils and fats, fat-soluble vitamins, various bioactive substances, seasonings, antioxidants, and preservatives. Examples of the colorant include carotene, flavonoid, turmeric, annatto, anthocyanin, and tar pigments. Examples of the flavoring agent include natural flavoring agent materials such as oleoresin and essential oils, and synthetic flavoring agent materials such as esters, ketones and lactones thereof. Examples of the oil and fat include animal and vegetable oils and fats, those derived from microorganisms, and synthetic oils and fats such as a medium-chain triacylglycerol. Examples of the fat-soluble vitamin include vitamins A, D, E, and K. Examples of the bioactive substance include coenzyme Q10, α-lipoic acid, astaxanthin, anthocyanin, lycopene, octacosanol, γ-oryzanol, turmeric (curcumin), phytosterol, and lutein. Examples of the seasoning include animal and vegetable extracts such as a pepper extract. Examples of the antioxidant include tocopherol, L-ascorbyl stearate, dibutyl hydroxytoluene (BHT), butyl hydroxyanisole (BHA), and antioxidative natural extracts. Examples of the preservative include parahydroxybenzoate and benzoic acid.

Examples of the emulsifier E1 include polyglycerol fatty acid esters having an HLB (Hydrophile-Lipophile Balance) of not less than 10, composed of esters of fatty acids having not more than 14 carbon atoms with polyglycerols having a polymerization degree of not less than 3. Polyglycerol fatty acid monoesters composed of a saturated or unsaturated fatty acid having 15 or more carbon atoms with polyglycerols (JP-A-10-084887, JP-A-11-332463) hardly make a solution stable when added to an aqueous medium. The fatty acid having not more than 14 carbon atoms may be either saturated or unsaturated, and preferably has 8 to 14 carbon atoms. The saturated or unsaturated fatty acid having 8 to 14 carbon atoms is preferably caprylic acid, pelargonic acid, capric acid, undecylic acid, lauric acid, tridecylic acid, myristic acid, or undecylenic acid, etc. Among them, caprylic acid, capric acid, lauric acid, and myristic acid are more preferable. The fatty acid having not more than 14 carbon atoms may be used alone or in combination of two or more.

The polyglycerol having a polymerization degree of not less than 3 is preferably a polyglycerol having a polymerization degree of from 3 to 10. The polyglycerol(s) may be used alone or in combination of two or more.

The HLB is a value representing a degree of affinity of an emulsifier for water and an oil-soluble substance. The HLB of the emulsifier E1 is preferably not less than 10. If the HLB is too low, the resultant solubilized composition containing an oil-soluble substance inhibits solubility of the composition in an aqueous medium when being added to the aqueous medium. The upper limit of the HLB is generally about 20.

A method of measuring the HLB will be described in Examples.

Among commercially available emulsifiers, preferred examples of the emulsifier E1 include decaglycerol monomyristate, decaglycerol monolaurate, hexaglycerol monolaurate, tetraglycerol monolaurate, decaglycerol monocaprate, and decaglycerol monocaprylate. Among them, decaglycerol monomyristate and decaglycerol monocaprate are more preferred.

As the emulsifier E1, those emulsifier(s) may be used alone or in combination of two or more.

In the present invention, a polymerization degree of the polyglycerol can be determined from a measured hydroxyl value according to the following calculation formula:

$$\text{hydroxyl value} = \frac{56110 \times (\text{polymerization degree} + 2)}{74 \times \text{polymerization degree} + 18}$$

When the emulsifier E1 is added, an amount added is preferably about 0.1 to 50 parts by mass, more preferably about 0.2 to 40 parts by mass, and still more preferably about 0.5 to 40 parts by mass to 1 part by mass of the oil-soluble substance, considering a solubilizing effect of the emulsifier E1 and a content of the oil-soluble substance. If the amount added of the emulsifier E1 is too small, it is difficult to stably solubilize the oil-soluble substance. On the contrary, if the amount added is too large, further enhancement of the effect of the present invention can hardly achieved, rather may cause a disadvantage of a reduced content of the oil-soluble substance.

Examples of the emulsifier E2 include sucrose fatty acid esters having an HLB of not less than 10 composed of an ester of fatty acids having not more than 14 carbon atoms with sucrose. The fatty acid having not more than 14 carbon atoms is similarly defined as the fatty acid having not more than 14 carbon atoms of the emulsifier E1. Appropriate sucrose fatty acid esters have no specific limitation. Among commercially available sucrose fatty acid esters, specific examples include sucrose myristate, sucrose laurate, sucrose caprylate, and sucrose caprate, in which monoesters account for 50% or more. Sucrose fatty acid esters of a fatty acid having not less than 15 carbon atoms or having an HLB of less than 10 (JP-A-10-43573, JP-A-10-66860) hardly make a solution stable when the composition is added to an aqueous medium. An HLB of the emulsifier E2 is preferably not less than 10. When the HLB is less than 10, the resultant solubilized composition containing an oil-soluble substance inhibits solubility of the composition in an aqueous medium when being added to the aqueous medium.

As the emulsifier E2, those emulsifier(s) may be used alone or in combination of two or more.

When the emulsifier E2 is added, an amount added is preferably about 0.1 to 30 parts by mass, more preferably about 0.2 to 25 parts by mass, and still more preferably about 0.5 to 25 parts by mass to 1 part by mass of the oil-soluble substance, considering a solubilizing effect of the emulsifier E2 and a content of the oil-soluble substance. If the amount added of the emulsifier E2 is too small, it is difficult to stably solubilize the oil-soluble substance. On the contrary, if the amount added thereof is too large, further enhancement of the effect of the present invention can be hardly achieved.

Examples of lecithin in which phosphatidylcholine (hereinafter, abbreviated to PC) accounts for 50% or more (hereinafter, abbreviated to PC≥50%) used as the emulsifier E3 in the present invention include normal lecithins obtained in a degumming step in production of a vegetable oil. Examples of such lecithin include vegetable lecithins such as a rapeseed lecithin and a soybean lecithin processed to increase a percentage of PC relative to a phospholipid content to 50% or more, and an egg lecithin derived from egg yolk. The vegetable lecithin contains constituent phospholipids other than PC such as phosphatidylethanolamine, phosphatidyl inositol, and phosphatidic acid, which are preferably removed off. The vegetable lecithin of PC≥50% (e.g., soybean lecithin) can be obtained by, for example, treating a normal vegetable lecithin with acetone, treating an acetone-insoluble fraction with ethanol, and evaporating ethanol from an ethanol-soluble fraction, thereby obtaining a vegetable lecithin of PC≥50% (e.g., soybean fractionated lecithin).

Examples of lysolecithin in which lysophosphatidylcholine (hereinafter, abbreviated to LPC) accounts for 50% or more used as the emulsifier E3 in the present invention include those containing LPC in a percentage of 50% or more relative to a lysophospholipid content obtained by the steps including enzymatically decomposing vegetable lecithins, such as a rapeseed lecithin and a soybean lecithin, and an egg lecithin derived from egg yolk with a phospholipase A1, A2, or the like, and solvent-fractionating or the like so as to increase a percentage of LPC to 50% or more.

The lysolecithin is preferably an egg lecithin as is, or is preferably obtained by enzymatically decomposing the vegetable lecithin of PC≥50% or enzymatically decomposing a normal vegetable lecithin to obtain from an ethanol-soluble fraction. Enzymatic decomposition can be conducted by or according to the known method. Examples of the method include a method of hydrolysis by heating an aqueous solution containing an egg lecithin or a vegetable lecithin of PC≥50% to about 50 to 60° C. and treating with a phospholipase A1 or A2.

In the present invention, a lecithin amount can be represented in terms of an amount of acetone-insoluble phospholipid. The amount of the phospholipid can be measured by, for example, a method described in "Kijun Yushi Bunseki Shiken Hou (Standard Methods for the Analysis of Fats, Oils and Related Materials), 5.3.3.1-86, Rin Shishitsu Rin Sosei (phospholipid and phosphorous composition)", Japan Oil Chemists' Society.

The lecithin in which a percentage of PC relative to a phospholipid content is 50% or more and the lysolecithin in which a percentage of LPC relative to a phospholipid content is 50% or more may be used alone or in combination thereof. The reason that a percentage of PC or LPC relative to a phospholipid content is 50% or more is that a too low percentage of PC or LPC relative to a phospholipid content causes the resultant solubilized composition containing an oil-soluble substance to inhibit solubility and transparency of the composition.

When the emulsifier E3 is added, an amount added is preferably about 0.1 to 20 parts by mass, more preferably about 0.2 to 15 parts by mass, and still more preferably about 0.5 to 15 parts by mass to 1 part by mass of the oil-soluble substance, considering a solubilizing effect of the emulsifier E3 and a content of the oil-soluble substance. If the content of the emulsifier E3 is too small, it is difficult to stably solubilize the oil-soluble substance, and if the content thereof is too large, further enhancement of the effect of the present invention can be hardly achieved, rather may cause a disadvantage of a reduced content of the oil-soluble substance, and in addition, may affect flavor.

In the step 1, the oil-soluble substance and two or three emulsifiers selected from the emulsifier E1, E2 or E3 are preferably transparently dissolved in (a) ethanol or (b) a mixed solvent of ethanol with one or more solvent(s) selected from acetone, hexane, and ethyl acetate. Examples of a combination of two or three emulsifiers selected from the emulsifier E1, E2 or E3 include: (i) a combination of the emulsifiers E1 and E2; (ii) a combination of the emulsifiers E1 and E3; (iii) a combination of the emulsifiers E2 and E3; and (iv) a combination of the emulsifiers E1, E2 and E3. Among them, the combination (iv) is particularly preferred.

A mixing ratio of the emulsifiers is, for example, in the combination (iv), preferably about 0.1 to 50 parts by mass of the emulsifier E1, about 0.1 to 30 parts by mass of the emulsifier E2, and about 0.1 to 20 parts by mass of the emulsifier E3, more preferably about 0.2 to 40 parts by mass of the emulsifier E1, about 0.2 to 25 parts by mass of the emulsifier E2, and about 0.2 to 15 parts by mass of the emulsifier E3, and still more preferably about 0.5 to 40 parts by mass of the emulsifier E1, about 0.5 to 25 parts by mass of the emulsifier E2, and about 0.5 to 15 parts by mass of the emulsifier E3 to 1 part by mass of the oil-soluble substance.

In the step 1, ethanol used has no specific limitation. Preferred examples of such ethanol include absolute ethanol (about 99% by volume or more) and industrial ethanol (about 95% by volume or more).

A preferred combination of the solvents used in the step 1 is ethanol, a mixed solvent of ethanol and acetone, or a mixed solvent of ethanol and hexane, provided that a percentage of ethanol in the solvent is not less than 50 (V/V) %.

Examples of the mixed solvent of ethanol with at least one selected from the group consisting of acetone, hexane and ethyl acetate include mixed solvents of ethanol with acetone, ethanol with hexane, ethanol with ethyl acetate, ethanol with acetone and hexane, ethanol with acetone and ethyl acetate, ethanol with hexane and ethyl acetate, and ethanol with acetone, hexane and ethyl acetate. Among them, preferred mixed solvents are those of ethanol with acetone, ethanol with hexane, ethanol with ethyl acetate, and ethanol with acetone and hexane, and more preferred mixed solvents are those of ethanol with acetone, and ethanol with hexane.

A mixing ratio of ethanol to other solvents is preferably from about 50 (V/V) % or more to less than about 100 (V/V) % of ethanol and the rest part of other solvents, more preferably from about 60 (V/V) % or more to about 90 (V/V) % or less of ethanol and the rest part of other solvents, and still more preferably from about 65 (V/V) % or more to about 80 (V/V) % or less of ethanol and the rest part of other solvents. Use of such a mixed solvent makes dissolution of the oil-soluble substance easier, and therefore a transparent solution of the oil-soluble substance and the emulsifiers can be obtained with a less amount of solvent.

An amount used of ethanol or the mixed solvent in the step 1 is, although varied according to types of the oil-soluble substance and the emulsifiers, preferably within the range of about 3 to 500 parts by mass, more preferably within the range of about 5 to 400 parts by mass, and still more preferably within the range of about 10 to 300 parts by mass to 1 part by mass of the oil-soluble substance. Within the range as described above, the oil-soluble substance and the emulsifiers can be transparently dissolved.

Dissolution of the oil-soluble substance and the emulsifiers in the step 1 is preferably conducted at room temperature or under a heating condition at about 50 to 60° C. The dissolution of the oil-soluble substance and the emulsifiers may be conducted with stirring optionally. Stirring can be performed with a known stirrer, for example, a common propeller stirrer. In the present invention, the "transparent" solution may be colored and a color tone of the solution may be determined depending on a type, an amount, and the like of the oil-soluble substance.

In the step 1, lower alcohols such as methanol, 1-propanol, 2-propanol, and 1-butanol may also be used instead of ethanol. In this case, ethanol may be replaced partially or wholly.

The solvent used in the step 1 may also contain water within the range not departing from the object of the present invention as long as the oil-soluble substance and the emulsifiers are transparently dissolved in the solvent. The method for preparation using such a solvent containing water is also within the scope of the present invention.

In the method for preparation of the present invention, the solution of the oil-soluble substance and two or three emulsifiers selected from the emulsifiers E1, E2, or E3 transparently dissolved in the solvent in the step 1 may further be added with a polyhydric alcohol optionally. The polyhydric alcohol is an alcohol having two or more hydroxyl groups in one molecule. Specific examples of the polyhydric alcohol include propylene glycol, glycerol, and sugar alcohols such as erythritol, sorbitol, maltitol and reduced starch syrup. Those polyhydric alcohol(s) may be used alone or in combination of two or more. An amount added of the polyhydric alcohol is, although it may be varied according to a type of the polyhydric alcohol, and types and amounts of the oil-soluble substance and the emulsifiers E1, E2, and E3 to be used for preparing the solubilized composition containing an oil-soluble substance, preferably within the range capable of maintaining transparency of the solution prepared as a transparent solution in the step 1. The range as described above is generally preferably not more than about 50 parts by mass, more preferably from about 0.5 to 20 parts by mass, and still more preferably from about 1 to 10 parts by mass to 1 part by mass of the oil-soluble substance. The polyhydric alcohol may be added to the solvent used in the step 1, or to the solution of the oil-soluble substance and the emulsifiers dissolved in the solvent.

The solubilized composition containing an oil-soluble substance prepared by further adding the polyhydric alcohol is easy to handle, and can have increased solubility in an aqueous medium.

Distillation off of the solvent in the step 2 of the present invention can be conducted by any method without limitation. Examples of the method include distillation under a reduced pressure of not more than about 20 mmHg with heating at about 40 to 60° C. After distillation off of the solvent, the composition is preferably substantially free of the solvent, or preferably does not contain all of the above-described solvents used for transparently dissolving the oil-soluble substance and two or three emulsifiers selected from the emulsifier E1, E2, or E3. The composition after distillation off of the solvent is preferably composed of (1) the oil-soluble substance and two or three emulsifiers selected from the emulsifier E1, E2, or E3; or (2) the oil-soluble substance, two or three emulsifiers selected from the emulsifier E1, E2, or E3, and the polyhydric alcohol optionally added.

The solubilized composition containing an oil-soluble substance prepared according to the method for preparation of the present invention is, when added to an aqueous medium, easily dissolved and uniformly dispersed in the aqueous medium.

The solubilized composition containing an oil-soluble substance prepared according to the method for preparation of the present invention has acid resistance and heat resistance, and can maintain the acid resistance and the heat resistance in an aqueous medium to which the solubilized composition containing an oil-soluble substance is added. As used herein, "acid resistance" means that the composition is stable under an acidic condition, and includes, for example, the state that the oil-soluble substance does not separate from the acidic aqueous medium. Examples of the acidic aqueous medium include an aqueous citric acid solution, fruit juices, and acetic acid of about pH 3 to 5. As used herein, "heat resistance" means that the composition is stable under a high temperature condition such as when subjected to a high temperature sterilization or placed under a high temperature environment. Examples of the high temperature sterilization generally include high temperature sterilizations at about not less than 100° C. such as a high-pressure steam sterilization using an autoclave set to about 120 to 125° C. and a moist heat sterilization using a multi-plate heater set to about 130° C. to 150° C. Examples of the high temperature environment include a situation that a food and drink is stored in a warmer set to about 50 to 80° C.

The solubilized composition containing an oil-soluble substance prepared according to the method for preparation of the present invention preferably include: (i) a solubilized composition containing the oil-soluble substance and the emulsifiers E1 and E2 in amounts of about 0.1 to 50 parts by mass and about 0.1 to 30 parts by mass, respectively, to 1 part by mass of the oil-soluble substance; (ii) a solubilized composition containing the oil-soluble substance and the emulsifiers E1 and E3 in amounts of about 0.1 to 50 parts by mass and about 0.1 to 20 parts by mass, respectively, to 1 part by mass of the oil-soluble substance; (iii) a solubilized composition containing the oil-soluble substance and the emulsifiers E2 and E3 in amounts of about 0.1 to 30 parts by mass and about 0.1 to 20 parts by mass, respectively, to 1 part by mass of the oil-soluble substance; and (iv) a solubilized composition containing the oil-soluble substance and the emulsifiers E1, E2 and E3 in amounts of about 0.1 to 50 parts by mass, about 0.1 to 30 parts by mass and about 0.1 to 20 parts by mass, respectively, to 1 part by mass of the oil-soluble substance. Among them, the composition (iv) is particularly preferred.

The solubilized composition containing an oil-soluble substance prepared according to the method for preparation of the present invention may further contain ethanol. In this case, ethanol is contained in any amount, but preferably not more than about 50 parts by mass, more preferably not more than about 40 parts by mass, and still more preferably not more than about 30 parts by mass to 1 part by mass of the oil-soluble substance. Addition of ethanol makes handling of the solubilized composition containing an oil-soluble substance easier. For example, the solubilized composition containing an oil-soluble substance that further contains ethanol may be, when added to an aqueous medium, more easily dissolved and dispersed in the aqueous medium.

When the solubilized composition containing an oil-soluble substance prepared according to the method for preparation of the present invention contains ethanol, a necessary amount of ethanol may be left in the composition after distillation off of the solvent in the step 2, or may be added to the composition after distillation off of the solvent in the step 2.

The solubilized composition containing an oil-soluble substance prepared according to the method for preparation of the present invention may further contain an emulsifier other than the emulsifiers E1, E2, and E3 within the range of not impairing the effect of the present invention. Specific examples of another emulsifier include polyglycerol fatty acid esters other than the emulsifier E1, sucrose fatty acid esters other than the emulsifier E2, lecithins and lysolecithins other than the emulsifier E3, other organic acid esters of monoglycerides, sorbitan fatty acid esters, propylene glycol fatty acid esters, saponin, sterol, cholic acid, deoxycholic acid, a yucca extract. These emulsifier(s) may be added alone or in combination of two or more.

The solubilized composition containing an oil-soluble substance prepared according to the method for preparation of the present invention can be ingested as a solution in water without further processing, or used as a raw material for foods and drinks and cosmetics. When the solubilized composition containing an oil-soluble substance prepared according to the method for preparation of the present invention is used as a raw material for foods and drinks and cosmetics and added to an aqueous medium, the composition can be made soluble only by light stirring. The solubilization includes both of formation of a thermodynamically stable solution of the solubilized composition containing an oil-soluble substance by dispersion of the composition in the aqueous medium, and formation of an uniform mixture of an oil phase and a water phase like as a microemulsion. The aqueous medium added with the solubilized composition containing an oil-soluble substance according to, the present invention can be a transparent solution, or a stable solution lacking transparency but that will not make the oil-soluble substance depositing or floating.

When the solubilized composition containing an oil-soluble substance prepared according to the method for preparation of the present invention is used as a raw material for foods and drinks and cosmetics, the composition is preferably diluted by about 30 to 5000 times.

The solubilized composition containing an oil-soluble substance of the present invention can be used in any food and drink. Examples of the food and drink include sports beverages containing at least one ingredient selected from minerals such as a table salt, acidulants, sweeteners, alcohols, vitamins, flavors, or fruit juices, and other beverages such as cow milk, soy milk, and fruit juices, acidic beverages such as black vinegar, lactobacillus beverages, carbonated beverages, alcoholic beverages, and nutritious beverages containing vitamins, minerals, and vegetable extracts such as those from turmeric. Examples of the common food include processed foods such as bread, confectionery, yogurt, dressing, soup, miso soup, and stew, and seasonings such as soy source and broth. When the solubilized composition containing an oil-soluble substance of the present invention is used in a drink, the drink can keep a uniform emulsified or solubilized state without causing creaming and/or separation of an oil-soluble ingredient for a long period of storage. The drink containing the solubilized composition containing an oil-soluble substance of the present invention can be subjected to a sterilizing treatment at a temperature of about 90 to 120° C.

The solubilized composition containing an oil-soluble substance of the present invention can be used in any cosmetic. Examples of the cosmetic include detergents, shampoos, rinses, hair tonics, hair lotions, after-shave lotions, body lotions, cosmetic lotions, cleansing lotions, massage creams, emollient creams, aerosol products, air refreshers, fragrances, deodorants, and bath agents.

The solubilized composition containing an oil-soluble substance of the present invention can be easily uniformly mixed with or dissolved in aqueous foods and drinks and cosmetics. The composition therefore can solubilize an oil-soluble substance in aqueous foods and drinks and cosmetics. The solubilized composition containing an oil-soluble substance of the present invention is, when added to an aqueous medium, uniformly solubilized in the aqueous medium only by light stirring without an emulsifying apparatus or a high-pressure homogenizer which applies strong shearing force. The solubilized composition containing an oil-soluble substance of the present invention has good acid resistance, and therefore an aqueous food and drink or cosmetic added with the solubilized composition containing an oil-soluble substance of the present invention can remain stable without causing separation of the oil-soluble substance even when the aqueous food and drink or cosmetic is an acidic solution containing an acid such as citric acid. The solubilized composition containing an oil-soluble substance of the present invention has good heat resistance, and therefore an aqueous food and drink or cosmetic added with the solubilized composition containing an oil-soluble substance of the present invention can remain stable without causing separation of the oil-soluble substance even when the aqueous food and drink or cosmetic is subjected to a high temperature sterilization when it needs the high temperature sterilization.

The present invention also provides use of the composition as a solubilizer of the oil-soluble substance for foods and drinks or cosmetics, wherein the composition is prepared by a method including: the step of dissolving the oil-soluble substance and two or three emulsifiers selected from (1) the emulsifier E1 containing an ester of a fatty acid having an HLB of not less than 10 and not more than 14 carbon atoms with a polyglycerol having a polymerization degree of not less than 3, (2) the emulsifier E2 containing an ester of a fatty acid having an HLB of not less than 10 and not more than 14 carbon atoms with sucrose, or (3) the emulsifier E3 containing lecithin in which phosphatidylcholine accounts for not less than 50% and/or lysolecithin in which lysophosphatidylcholine accounts for not less than 50% of a phospholipid content in (a) ethanol or (b) a mixed solvent of ethanol with at least one selected from the group consisting of acetone, hexane, and ethyl acetate to prepare a transparent solution; and the step of distilling the solvent off from the transparent solution.

DETAILED DESCRIPTION OF THE INVENTION

Hereinafter, the present invention will be described in more detail with reference to Examples, but should not be limited by the Examples.

The present invention can be varied, modified, or improved based on the knowledge of those skilled in the art within the spirit and scope not deviating from those of the invention, in addition to the following Examples and further the aforementioned specific descriptions. In Examples, the "percentage" means "% by mass".

Emulsifiers used in Examples were the following commercial products.

Decaglycerol monomyristate: Glyster MM-750, manufactured by Sakamoto Yakuhin Kogyo Co., Ltd. (polymerization degree 10, HLB 15.5)

Decaglycerol monolaurate: Glyster ML-750, manufactured by Sakamoto Yakuhin Kogyo Co., Ltd. (polymerization degree 10, HLB 14.8)

Decaglycerol monocaprate: Glyster MD-750, manufactured by Sakamoto Yakuhin Kogyo Co., Ltd. (polymerization degree 10, HLB 15.0)

Decaglycerol monostearate: Glyster MSW-7S, manufactured by Sakamoto Yakuhin Kogyo Co., Ltd. (polymerization degree 10, HLB 13.4)

Decaglycerol monooleate: Glyster MO-7S, manufactured by Sakamoto Yakuhin Kogyo Co., Ltd. (polymerization degree 10, HLB 12.9)

Decaglycerol monopalmitate: Ryoto P-8D, manufactured by Mitsubishi-Kagaku Foods Corporation (polymerization degree 10, HLB 16)

Tetraglycerol monolaurate: Glyster ML-310, manufactured by Sakamoto Yakuhin Kogyo Co., Ltd. (polymerization degree 4, HLB 10.3)

Diglycerol monomyristate: Poem DM-100, manufactured by Riken Vitamin Co., Ltd. (polymerization degree 2, HLB 8.8)

Sucrose laurate (monoester 80%): Ryoto L-1695, manufactured by Mitsubishi-Kagaku Foods Corporation (HLB 16)

Sucrose laurate (monoester 30%): Ryoto L-595, manufactured by Mitsubishi-Kagaku Foods Corporation (HLB 5)

Sucrose myristate (monoester 80%): Ryoto M-1695, manufactured by Mitsubishi-Kagaku Foods Corporation (HLB 16)

Sucrose oleate (monoester 70%): Ryoto O-1570, manufactured by Mitsubishi-Kagaku Foods Corporation (HLB 15)

Sucrose palmitate (monoester 80%): Ryoto P-1670, manufactured by Mitsubishi-Kagaku Foods Corporation (HLB 16)

Sorbitol monolaurate: Poem L-300, manufactured by Riken Vitamin Co., Ltd. (HLB 8.0)

Sorbitan monolaurate: Emasol L-10V, manufactured by Kao Corporation (HLB 8.6)

Soybean lecithin: SLP-paste, manufactured by Tsuji Oil Mill Co., Ltd. (acetone-insoluble matter (phospholipid content): 62% by mass (percentage of PC to phospholipid: 28%))

Soybean fractionated lecithin PC35: SLP-PC35, manufactured by Tsuji Oil Mill Co., Ltd. (acetone-insoluble matter (phospholipid content): 65% by mass (percentage of PC to phospholipid: 70%))

Soybean fractionated lysolecithin LPC70: SLP-LPC70, manufactured by Tsuji Oil Mill Co., Ltd. (acetone-insoluble matter (phospholipid content): 98% by mass (percentage of LPC to lysophospholipid: 76%))

In Examples, an HLB value was calculated using the following Griffin's equation.

$$HLB = 20 \times (1 - SV/NV)$$

SV: saponification value of an ester
NV: neutralization value of a raw material fatty acid

Example 1

| | |
|---|---|
| Turmeric (Curcumin C3 Complex, manufactured by Sabinsa Japan Corporation, purity: 96.95%, the same turmeric was used in the following Examples) | 2.5 g |
| Decaglycerol monomyristate | 92.5 g |
| Soybean fractionated lecithin PC35 | 5.0 g |

Turmeric, decaglycerol monomyristate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a paste.

Example 2

100 g of a solubilized composition as a semi-solid was similarly obtained as in Example 1, except that 5 g of soybean fractionated lysolecithin LPC70 was used instead of 5 g of soybean fractionated lecithin PC35 in Example 1.

Example 3

100 g of a solubilized composition as a semi-solid was similarly obtained as in Example 1, except that 2 g of soybean fractionated lecithin PC35 and 3 g of soybean fractionated lysolecithin LPC70 were used instead of 5 g of soybean fractionated lecithin PC35 in Example 1.

Example 4

| | |
|---|---|
| Turmeric | 2.5 g |
| Decaglycerol monolaurate | 92.5 g |
| Soybean fractionated lecithin PC35 | 5.0 g |

Turmeric, decaglycerol monolaurate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a paste.

Example 5

100 g of a solubilized composition as a semi-solid was similarly obtained as in Example 4, except that 5 g of soybean fractionated lysolecithin LPC70 was used instead of 5 g of soybean fractionated lecithin PC35 in Example 4.

Example 6

| Turmeric | 2.5 g |
| Decaglycerol monocaprate | 92.5 g |
| Soybean fractionated lecithin PC35 | 5.0 g |

Turmeric, decaglycerol monocaprate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a paste.

Example 7

100 g of a solubilized composition as a semi-solid was similarly obtained as in Example 6, except that 5 g of soybean fractionated lysolecithin LPC70 was used instead of 5 g of soybean fractionated lecithin PC35 in Example 6.

Example 8

| Turmeric | 2.5 g |
| Tetraglycerol monolaurate | 92.5 g |
| Soybean fractionated lecithin PC35 | 5.0 g |

Turmeric, tetraglycerol monolaurate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a paste.

Example 9

100 g of a solubilized composition as a semi-solid was similarly obtained as in Example 8, except that 5 g of soybean fractionated lysolecithin LPC70 was used instead of 5 g of soybean fractionated lecithin PC35 in Example 8.

Example 10

| Turmeric | 2.5 g |
| Sucrose myristate | 92.5 g |
| Soybean fractionated lecithin PC35 | 5.0 g |

Turmeric, sucrose myristate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a paste.

Example 11

100 g of a solubilized composition as a semi-solid was similarly obtained as in Example 10, except that 5 g of soybean fractionated lysolecithin LPC70 was used instead of 5 g of soybean fractionated lecithin PC35 in Example 10.

Example 12

| Turmeric | 2.5 g |
| Sucrose laurate (L-1695) | 92.5 g |
| Soybean fractionated lecithin PC35 | 5.0 g |

Turmeric, sucrose laurate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a paste.

Example 13

100 g of a solubilized composition as a semi-solid was similarly obtained as in Example 12, except that 5 g of soybean fractionated lysolecithin LPC70 was used instead of 5 g of soybean fractionated lecithin PC35 in Example 12.

Example 14

| Turmeric | 2.5 g |
| Decaglycerol monomyristate | 92.5 g |
| Sucrose laurate (L-1695) | 5.0 g |

Turmeric, decaglycerol monomyristate, and sucrose laurate were added to 500 g of ethanol (99% by volume) and dissolved with heating to 60° C. for 10 minutes. Then, ethanol was distilled off under reduced pressure to give 100 g of a solubilized composition as a paste.

Example 15

| Turmeric | 2.5 g |
| Decaglycerol monomyristate | 90.0 g |
| Sucrose laurate (L-1695) | 5.0 g |
| Soybean fractionated lecithin PC35 | 2.5 g |

Turmeric, decaglycerol monomyristate, sucrose laurate, and soybean fractionated lecithin PC35 were added to 500 g of ethanol (99% by volume) and dissolved with heating to 60° C. for 10 minutes. Then, ethanol was distilled off under reduced pressure to give 100 g of a solubilized composition as a semi-solid.

Comparative Examples 1 to 11

Compositions of Comparative Examples 1 to 11 were similarly prepared as in Example 1, except that emulsifiers in the following Table 1 were used instead of decaglycerol monomyristate and soybean fractionated lecithin PC35 in Example 1.

TABLE 1

| Comparative Example | Emulsifier |
|---|---|
| 1 | Decaglycerol monomyristate 97.5 g |
| 2 | Decaglycerol monomyristate 92.5 g and soybean lecithin 5.0 g |
| 3 | Decaglycerol monostearate 92.5 g and soybean fractionated lecithin PC35 5.0 g |
| 4 | Decaglycerol monooleate 92.5 g and soybean fractionated lecithin PC35 5.0 g |
| 5 | Decaglycerol monopalmitate 92.5 g and soybean fractionated lecithin PC35 5.0 g |
| 6 | Diglycerol monomyristate 92.5 g and soybean fractionated lecithin PC35 5.0 g |
| 7 | Sucrose oleate 92.5 g and soybean fractionated lecithin PC35 5.0 g |
| 8 | Sucrose palmitate 92.5 g and soybean fractionated lecithin PC35 5.0 g |
| 9 | Sucrose laurate (L-595) 92.5 g and soybean fractionated lecithin PC35 5.0 g |
| 10 | Sorbitol monolaurate 92.5 g and soybean fractionated lecithin PC35 5.0 g |
| 11 | Sorbitan monolaurate 92.5 g and soybean fractionated lecithin PC35 5.0 g |

Example 16

| | |
|---|---|
| Turmeric | 2.5 g |
| Decaglycerol monomyristate | 92.5 g |
| Soybean fractionated lecithin PC35 | 5.0 g |

Turmeric, decaglycerol monomyristate, and soybean fractionated lecithin PC35 were added to 500 g of 70% ethanol (containing 30% of water) and dissolved with heating to 60° C. for 10 minutes. After confirming that the solution became transparent, 70% ethanol was distilled off under reduced pressure to give 100 g of a composition as a hard paste.

Comparative Example 12

A mixture was similarly prepared and heated at 60° C. as in Example 16, except that an aqueous solution of 50% ethanol was used instead of 70% ethanol in Example 16. The heated solution did not become transparent in 10 minutes and was opaque, containing a small amount of insoluble matter. After further heating for one hour, the mixture was still opaque. Then, the aqueous solution of 50% ethanol was distilled off under reduced pressure to give 100 g of a composition as a nonuniform paste.

Example 17

| | |
|---|---|
| Turmeric | 2.5 g |
| Decaglycerol monomyristate | 92.5 g |
| Soybean fractionated lecithin PC35 | 5.0 g |

Turmeric, decaglycerol monomyristate, and soybean fractionated lecithin PC35 were dissolved in 100 g of acetone. The mixture was added to 200 g of ethanol (99% by volume), and stirred to give a transparent solution. Solvents were distilled off under reduced pressure to give 100 g of a composition as a hard paste.

Example 18

| | |
|---|---|
| Turmeric | 2.5 g |
| Decaglycerol monomyristate | 92.5 g |
| Soybean fractionated lecithin PC35 | 5.0 g |
| Ethanol | 5.0 g |

Turmeric, decaglycerol monomyristate, and soybean fractionated lecithin PC35 were added to 500 g of ethanol (99% by volume) and dissolved with heating to 60° C. over 10 minutes. After confirming that the solution became transparent, ethanol was distilled off under reduced pressure so as to leave 5 g of ethanol to give 105 g of a composition as a soft paste.

Example 19

| | |
|---|---|
| Turmeric | 2.5 g |
| Decaglycerol monomyristate | 92.5 g |
| Soybean fractionated lecithin PC35 | 5.0 g |
| Ethanol | 50.0 g |

Turmeric, decaglycerol monomyristate, and soybean fractionated lecithin PC35 were added to 500 g of ethanol (99% by volume) and dissolved with heating to 60° C. for 10 minutes. After confirming that the solution became transparent, ethanol was distilled off under reduced pressure so as to leave 50 g of ethanol to give 150 g of a viscous solution.

Example 20

| | |
|---|---|
| Turmeric | 2.5 g |
| Decaglycerol monomyristate | 92.5 g |
| Soybean fractionated lecithin PC35 | 5.0 g |
| Glycerol | 5.0 g |

Turmeric, decaglycerol monomyristate, and soybean fractionated lecithin PC35 were added to 500 g of ethanol (99% by volume), in which glycerol was dissolved, and dissolved with heating to 60° C. for 10 minutes. After confirming that the solution became transparent, ethanol was distilled off under reduced pressure to give 105 g of a composition as a soft paste.

Example 21

| | |
|---|---|
| Turmeric | 2.5 g |
| Decaglycerol monomyristate | 92.5 g |
| Soybean fractionated lecithin PC35 | 5.0 g |
| Maltitol | 5.0 g |

Turmeric, decaglycerol monomyristate, and soybean fractionated lecithin PC35 were added to 500 g of ethanol (99% by volume), in which maltitol was dissolved, and dissolved with heating to 60° C. for 10 minutes. After confirming that the solution became transparent, ethanol was distilled off under reduced pressure to give 105 g of a composition as a relatively hard paste.

Comparative Example 13

100 g of a composition was prepared from the same turmeric, decaglycerol monomyristate, and soybean fractionated lecithin PC35 as in Example 1, by kneading them for 30 minutes at 100° C. without dissolving in ethanol and without using a solvent.

Comparative Example 14

Turmeric, decaglycerol monomyristate, and soybean fractionated lecithin were added with stirring to 1 L of 70° C. warm water instead of ethanol in Example 1. After 10 minutes, the mixture was subjected to emulsification with a disperser (manufactured by Janke & Kunkel GmbH & Co. KG) at 24000 rounds for 10 minutes to give a milky white emulsion. The emulsion was concentrated under reduced pressure to give a composition as a nonuniform paste.

Test Example 1

Each of the compositions of Examples 1 to 15 and Comparative Examples 1 to 11 was added to water so that a concentration thereof was 5% and gently stirred as ordinarily done. The resultant aqueous solution was examined for transparency. The transparency was graded into the following three grades. The results are shown in Table 2.

Evaluation of Transparency:
○: transparently dissolved
Δ: dissolved but not transparent
x: contained insoluble matters floating or precipitating

TABLE 2

| Solubilized composition | Transparency of the aqueous solution |
|---|---|
| Example 1 | ○ |
| Example 2 | ○ |
| Example 4 | ○ |
| Example 5 | ○ |
| Example 6 | ○ |
| Example 7 | ○ |
| Example 8 | ○ |
| Example 9 | ○ |
| Example 10 | ○ |
| Example 11 | ○ |
| Example 12 | ○ |
| Example 13 | ○ |
| Example 14 | ○ |
| Example 15 | ○ |
| Comparative Example 1 | Δ |
| Comparative Example 2 | X |
| Comparative Example 3 | X |
| Comparative Example 4 | Δ |
| Comparative Example 5 | X |
| Comparative Example 6 | X |
| Comparative Example 7 | X |
| Comparative Example 8 | X |
| Comparative Example 9 | X |
| Comparative Example 10 | X |
| Comparative Example 11 | X |

Compositions containing polyglycerol esters of fatty acids having a polymerization degree of not less than 3, an HLB of not less than 10 and not more than 14 carbon atoms, soybean fractionated lecithins or soybean fractionated lysolecithins in which a percentage of PC or LPC was not less than 50%, and turmeric were transparently dissolved in the aqueous solution (Examples 1 to 9).

It was found that the polyglycerol fatty acid ester alone insufficiently functioned as an emulsifier (Comparative Example 1), and that the composition containing the polyglycerol fatty acid ester and a normal soybean lecithin resulted in an ethanol solution containing insoluble matters, and did not give a solubilized composition after distillation off of ethanol (Comparative Example 2).

Compositions containing polyglycerol esters of fatty acids having more than 14 carbon atoms including palmitic acid, oleic acid, and stearic acid also were inadequate as solubilized compositions even though the esters had an HLB of not less than 10 and the polyglycerols had a polymerization degree of not less than 3 (Comparative Examples 3 to 5).

The composition containing the fatty acid ester of the polyglycerol having a polymerization degree of less than 3 was not transparently dissolved in the aqueous solution even though the composition contained the polyglycerol ester of fatty acid having not more than 14 carbon atoms (Comparative Example 6).

Compositions containing sucrose esters of fatty acids having an HLB of not less than 10 and not more than 14 carbon atoms, soybean fractionated lecithins or soybean fractionated lysolecithins in which a percentage of PC or LPC was not less than 50%, and turmeric were transparently dissolved in the aqueous solution (Examples 10 to 13). Compositions containing esters of fatty acids having more than 14 carbon atoms including palmitic acid and oleic acid with polyglycerols having a polymerization degree of not less than 3, and the composition containing the polyglycerol ester of the fatty acid having not more than 14 carbon atoms including lauric acid but having an HLB of less than 10 did not transparently dissolve in the aqueous solution (Comparative Examples 7 to 9).

The composition containing the polyglycerol ester of the fatty acid having a polymerization degree of not less than 3, a 10 or more HLB and not more than 14 carbon atoms, the sucrose fatty acid ester, and turmeric was transparently dissolved in the aqueous solution without a soybean fractionated lecithin or soybean fractionated lysolecithin (Example 14). However, the composition further containing a soybean fractionated lecithin and a soybean fractionated lysolecithin had higher solubility and resulted in a more transparent solution (Example 15).

Compositions prepared by using sorbitol and sorbitan fatty acid esters other than polyglycerol fatty acid esters and sucrose fatty acid esters were not transparently dissolved in the aqueous solution (Comparative Examples 10 to 11).

Test Example 2

Heat and Acid Resistance Test of Solubilized Composition

Each of the solubilized compositions of Examples 2 and 3, and the composition of Comparative Example 1 was added and dissolved in water or a citric acid buffer of pH 3 so that a concentration of the composition was 5%. The mixtures were heat treated for 30 minutes at 120° C. when the solvent is water, and for 10 minutes at 110° C. when the solvent is the citric acid buffer of pH 3. The heat-treated solutions were stored for 30 days at 40° C., and examined for transparency. The transparency was evaluated into the following three grades. The results are shown in Table 3.

Evaluation of Transparency:
○: transparently dissolved
Δ: dissolved but not transparent
x: contained insoluble matters floating or precipitating

TABLE 3

| Composition | Water | | Citric acid buffer (pH 3) | |
|---|---|---|---|---|
| | Immediately after heating | 40° C. × 30 days | Immediately after heating | 40° C. × 30 days |
| Example 2 | ○ | ○ | ○ | ○ |
| Example 3 | ○ | ○ | ○ | ○ |
| Comparative Example 1 | X | X | X | X |

Solubilized compositions of Examples 2 and 3 of the present invention also had heat resistance and acid resistance, not only transparently dissolved and solubilized. The composition of Comparative Example 1 without a soybean fractionated lecithin or a soybean fractionated lysolecithin was inferior in terms of both acid and heat resistance.

Test Example 3

The following items were evaluated:
transparency of the compositions of Examples 1, 16, and 17, and Comparative Example 12 as a solution in a solvent after turmeric, decaglycerol monomyristate, and soybean fractionated lecithin PC35 were added to the solvent and heated before the solvent was distilled off;
state of the resultant compositions of Examples 1, 16, and 17, and Comparative Examples 12, 13, and 14; and
transparency of aqueous solutions prepared by adding the resultant compositions to the solutions so as to be 5% concentration, and stirring.
The transparency was evaluated into the following three grades. The results are shown in Table 4.
Evaluation of Transparency:
○: transparently dissolved
Δ: dissolved but not transparent
x: contained insoluble matters floating or precipitating

TABLE 4

| | Transparency of solution in solvent | State of composition | Transparency of aqueous solution |
|---|---|---|---|
| Example 1 | ○ | uniform paste | ○ |
| Example 16 | ○ | uniform paste | ○ |
| Example 17 | ○ | uniform paste | ○ |
| Comparative Example 12 | Δ | nonuniform paste | X |
| Comparative Example 13 | — | nonuniform paste | X |
| Comparative Example 14 | — | nonuniform paste | X |

Similar results were obtained by using a soybean fractionated lysolecithin LPC70 instead of the soybean fractionated lecithin PC35 in Examples 16 and 17, and Comparative Examples 12 to 14.

In the method for preparing a solubilized composition containing an oil-soluble substance of the present invention, when the solvent is ethanol (99% by volume) alone, or a mixed solvent of ethanol with 30% of water or acetone, a solution before distilling off of the solvent was transparent, and a composition obtained by distilling the solvent off was transparently dissolved in a solution when being added thereto (Examples 1, 16, and 17). However, when the solvent used was a 50% aqueous ethanol solution, a solution before distilling off of the solvent was not transparent, and a composition obtained by distilling off the solvent was not transparently dissolved in a solution (Comparative Example 12). Compositions prepared by only heat dissolving an oil-soluble substance with an emulsifier in the absence of solvent, and compositions prepared by emulsifying an oil-soluble substance with an emulsifier in water and concentrating were not dissolved in a solution and they floated or precipitated (Comparative Examples 13 and 14). These results clearly show that a composition prepared by transparently dissolving an oil-soluble substance and an emulsifier in a solvent and distilling off the solvent exhibits the effect of the present invention.

Test Example 4

Properties and Solubility Test of Solubilized Composition

Properties of the solubilized compositions of Examples 1 and 18 to 21, and solubility and transparency of mixtures prepared by adding the compositions to water so as to be 5% concentration and gently stirring were examined. The results are shown in Table 5.

TABLE 5

| | Properties | Solubility | Transparency |
|---|---|---|---|
| Example 1 | hard paste | dissolved within 3 minutes | transparent |
| Example 18 | soft paste | dissolved within 1 minute | transparent |
| Example 19 | viscous solution | immediately dissolved | transparent |
| Example 20 | soft paste | dissolved within 1 minute | transparent |
| Example 21 | relatively hard paste | dissolved within 1 minute | transparent |

Solubilized compositions containing a polyhydric alcohol such as ethanol, glycerol, and maltitol were in a soft paste form or a viscous solution, which are easy to handle. The solubilized compositions were quickly and transparently dissolved in water within 3 minutes, which shows that the solubilized compositions have excellent solubility in water (Examples 18 to 21).

INDUSTRIAL APPLICABILITY

The solubilized composition containing an oil-soluble substance according to the present invention is useful as a raw material for foods and drinks, cosmetics, and medicines.

What is claimed is:
1. A method for preparing a solubilized semi-solid or paste composition containing an oil-soluble substance having both acid and heat resistance, comprising:
a step of dissolving the oil-soluble substance and a combination of two or three emulsifiers selected from the group consisting of:
(1) one emulsifier E1 and one emulsifier E2;
(2) one emulsifier E1 and one emulsifier E3;
(3) one emulsifier E2 and one emulsifier E3; and
(4) one emulsifier E1, one emulsifier E2 and one emulsifier E3,
in a solvent which is (a) ethanol or (b) a mixed solvent of ethanol with at least one other solvent selected from the group consisting of acetone, hexane and ethyl acetate, to prepare a transparent solution; and
a step of distilling the solvent off of the transparent solution,
wherein:
the emulsifier E1 is one or more selected from the group consisting of:
(E1-1) decaglycerol monomyristate;
(E1-2) decaglycerol monolaurate;
(E1-3) tetraglycerol monolaurate;
(E1-4) decaglycerol monocaprate; and
(E1-5) hexaglycerol monolaurate,
the emulsifier E2, in which monoesters account for 50% or more, is:
(E2-1) sucrose myristate; and/or
(E2-2) sucrose laurate, and
the emulsifier E3 is one or more selected from the group consisting of:
(E3-1) soybean fractionated lecithin;
(E3-2) soybean fractionated lysolecithin;
(E3-3) rapeseed fractionated lecithin;
(E3-4) rapeseed fractionated lysolecithin;
(E3-5) sunflower fractionated lecithin; and
(E3-6) sunflower fractionated lysolecithin,
wherein the fractionated lecithin(s) contain not less than 50% of phosphatidylcholine relative to a phospholipid content, and wherein the fractionated lecithin(s) are obtained by a method comprising the steps of degumming in production of a vegetable oil to obtain a vegetable lecithin, treating the vegetable lecithin with acetone to obtain an acetone-insoluble fraction, treating the acetone-insoluble fraction with ethanol to obtain an ethanol-soluble fraction, and evaporating ethanol from the ethanol-soluble fraction,
wherein the fractionated lysolecithin(s) contain not less than 50% of lysophosphatidylcholine relative to a phospholipid content, and wherein the fractionated lysolecithin(s) are obtained by a method comprising a step of enzymatically decomposing vegetable lecithin containing phosphatidylcoline in an amount ≥50% with a phospholipase A1 or A2 or a step of enzymatically decomposing a vegetable lecithin to obtain an ethanol-soluble fraction, and
wherein the contents of the combination of two or three emulsifiers to 1 part by mass of the oil-soluble substance are:
for (1), 0.1 to 50 parts by mass for the emulsifier E1, and 0.1 to 30 parts by mass for the emulsifier E2;
for (2), 0.1 to 50 parts by mass for the emulsifier E1, and 0.1 to 20 parts by mass for the emulsifier E3;
for (3), 0.1 to 30 parts by mass for the emulsifier E2, and 0.1 to 20 parts by mass for the emulsifier E3; and
for (4), 0.1 to 50 parts by mass for the emulsifier E1, 0.1 to 30 parts by mass for the emulsifier E2, and 0.1 to 20 parts by mass for the emulsifier E3,
to obtain the solubilized semi-solid or paste composition.

2. The method according to claim 1, wherein the solvent is (a) ethanol or (b) a mixed solvent of ethanol with acetone or hexane, and a percentage of ethanol in the solvent (b) is 50 to less than 100 (V/V) %.

3. The method according to claim 1, further comprising:
a step of adding a polyhydric alcohol to the transparent solution in an amount of not more than 50 parts by mass to 1 part by mass of the oil-soluble substance, between the step of preparing the transparent solution and the step of distilling the solvent off of the transparent solution.

4. A solubilized semi-solid or paste composition containing an oil-soluble substance having both acid and heat resistance, wherein the composition is prepared by the method according to claim 1,
wherein the composition consists of the oil-soluble substance and the combination of two or three emulsifiers selected from the group consisting of:
(1) one emulsifier E1 and one emulsifier E2;
(2) one emulsifier E1 and one emulsifier E3;
(3) one emulsifier E2 and one emulsifier E3; and
(4) one emulsifier E1, one emulsifier E2 and one emulsifier E3,
wherein emulsifiers E1, E2 and E3 are as defined in claim 1,
wherein the composition further comprises ethanol in a proportion of not more than 50 parts by mass to 1 part by mass of the oil-soluble substance.

5. The method according to claim 1, wherein the combination of two or three emulsifiers is selected from the group consisting of:
(2) one emulsifier E1 and one emulsifier E3;
(3) one emulsifier E2 and one emulsifier E3; and
(4) one emulsifier E1, one emulsifier E2 and one emulsifier E3.

6. The method according to claim 1,
wherein the combination of emulsifiers is: (4) one emulsifier E1, one emulsifier E2 and one emulsifier E3.

7. The method according to claim 1,
wherein the emulsifier E1 is one or more selected from the group consisting of:
(E1-1) decaglycerol monomyristate;
(E1-2) decaglycerol monolaurate;
(E1-3) decaglycerol monocaprate; and
(E1-4) tetraglycerol monolaurate, and
wherein the emulsifier E3 is one or more selected from the group consisting of:
(E3-1) soybean fractionated lecithin;
(E3-2) soybean fractionated lysolecithin;
(E3-3) rapeseed fractionated lecithin; and
(E3-4) rapeseed fractionated lysolecithin.

8. The method according to claim 7,
wherein the emulsifier E3 is:
(E3-1) soybean fractionated lecithin; and/or
(E3-2) soybean fractionated lysolecithin.

9. The method according to claim 7,
wherein the combination of two or three emulsifiers is:
(4) one emulsifier E1, one emulsifier E2 and one emulsifier E3 and
wherein the emulsifier E3 is:
(E3-2) soybean fractionated lysolecithin; and/or
(E3-4) rapeseed fractionated lysolecithin.

10. The method according to claim 9,
wherein the emulsifier E3 is:
(E3-2) soybean fractionated lysolecithin.

11. The method according to claim 1,
wherein the combination of two or three emulsifiers is:
(4) one emulsifier E1, one emulsifier E2 and one emulsifier E3,
wherein the emulsifier E1 is one or more selected from the group consisting of:
(E1-1) decaglycerol monomyristate;
(E1-2) decaglycerol monolaurate;
(E1-3) decaglycerol monocaprate; and
(E1-4) tetraglycerol monolaurate, and
wherein the emulsifier E3 is one or more selected from the group consisting of:
(E3-2) soybean fractionated lysolecithin;
(E3-4) rapeseed fractionated lysolecithin; and
(E3-6) sunflower fractionated lysolecithin.

* * * * *